United States Patent [19]

Paparizos et al.

[11] Patent Number: 5,466,652
[45] Date of Patent: Nov. 14, 1995

[54] PROCESS FOR THE PREPARATION OF VINYL ACETATE CATALYST

[75] Inventors: Christos Paparizos, Willowick; Dev D. Suresh, Hudson, both of Ohio; Michael F. Lemanski, Chester, N.Y.

[73] Assignee: The Standard Oil Co., Cleveland, Ohio

[21] Appl. No.: 200,130

[22] Filed: Feb. 22, 1994

[51] Int. Cl.[6] .............................. B01J 23/04; B01J 23/44; B01J 23/52
[52] U.S. Cl. .......................... 502/330; 502/333; 502/344; 560/261
[58] Field of Search .................... 502/330, 344, 502/333; 560/261

[56] References Cited

U.S. PATENT DOCUMENTS

| | | |
|---|---|---|
| 3,117,990 | 1/1964 | Adachi et al. . |
| 3,686,287 | 8/1972 | Knights . |
| 3,743,607 | 7/1973 | Sennewald et al. . |
| 3,759,839 | 9/1973 | Fernholz et al. . |
| 3,761,513 | 9/1973 | Sennewald et al. . |
| 3,775,342 | 11/1973 | Kronig et al. . |
| 3,950,400 | 4/1976 | Fernholz et al. . |
| 3,969,271 | 7/1976 | Lester . |
| 4,048,096 | 9/1977 | Bissot . |
| 4,087,622 | 5/1978 | Nakamura et al. . |
| 4,188,490 | 2/1980 | Hinsenkamp et al. . |
| 4,517,377 | 5/1985 | Isshiki et al. . |
| 4,933,204 | 6/1990 | Warren, Jr. et al. . |
| 4,978,778 | 12/1990 | Isshiki et al. . |
| 5,051,394 | 9/1991 | Haruta et al. . |
| 5,179,056 | 1/1993 | Bartley . |
| 5,179,057 | 1/1993 | Bartley . |
| 5,185,308 | 2/1993 | Bartley et al. . |
| 5,189,004 | 2/1993 | Bartley ....................... 502/170 |
| 5,314,858 | 5/1994 | Colling . |

FOREIGN PATENT DOCUMENTS

| | | |
|---|---|---|
| 0403950 | 12/1990 | European Pat. Off. . |
| 687990 | 12/1968 | South Africa . |
| 1266624 | 3/1972 | United Kingdom . |
| 1266623 | 3/1972 | United Kingdom . |
| 1283737 | 8/1972 | United Kingdom . |
| 1500167 | 2/1978 | United Kingdom . |

OTHER PUBLICATIONS

T. Kawaguchi et al., Applied Catalysis, 36 (1988) 67–79.
T. Kawaguchi et al., *Applied Catalysis*, 32 (1987) 23–36.
T. Kawaguchi et al., J. Chem. Tech. Biotechnol., 42 (1988) 113–127.

Primary Examiner—Anthony McFarlane
Attorney, Agent, or Firm—Michael F. Esposito; David J. Untener

[57] ABSTRACT

A process for the manufacture of a Pd/Au/alkali metal catalyst, preferably a fluid bed catalyst used in the production of vinyl acetate comprising impregnating a microspheroidal support with a hydroxy-free metal salt solution of Pd and Au substantially free of barium and halide, reducing said salts to deposit Pd and Au on said support surface and impregnating said support with a halide-free metal salt of an alkali metal (preferably potassium).

12 Claims, No Drawings

PROCESS FOR THE PREPARATION OF VINYL ACETATE CATALYST

The present invention relates to a process of producing palladium/gold catalysts useful in effecting the production of vinyl acetate from ethylene, acetic acid and an oxygen containing gas. In particular, the present invention relates to the process of producing palladium-gold fluid bed catalyst useful in the manufacture of vinyl acetate.

The production of vinyl acetate by reacting ethylene, acetic acid and oxygen together in the gas-phase in the presence of a catalyst containing palladium, gold and an alkali metal acetate promoter is known. The catalyst components are typically supported on a porous carrier material such as silica or alumina.

In early examples of these catalysts, both the palladium and gold were distributed more or less uniformly throughout the carrier (see for example U.S. Pat. Nos. 3,275,680, 3,743,607 and 3,950,400 and GB 1333449 and So. African Patent No. 687990). This was subsequently recognized to be a disadvantage since it was found that the material within the inner part of the carrier did not contribute to the reaction since the reactants did not diffuse significantly into the carrier before reaction occurred. In other words, a significant amount of the palladium and gold never came into contact with the reactants.

In order to overcome this problem, new methods of catalyst manufacture were devised with the aim of producing catalysts in which the active components were concentrated in the outermost shell of the support (shell impregnated catalysts). For example, GB Patent No.1500167 claims catalysts in which at least 90% of the palladium and gold is distributed in that part of the carrier particle which is not more than 30% of the particle radius from the surface. GB Patent No. 1283737 teaches that the degree of penetration into the porous carrier can be controlled by pretreating the porous carrier with an alkaline solution of, for example, sodium carbonate or sodium hydroxide.

Another approach which has been found to produce particularly active catalysts is described in U.S. Pat. No. 4,048,096. In this patent shell impregnated catalysts are produced by a process comprising the steps of (1) impregnating a carrier with aqueous solutions of water-soluble palladium and gold compounds, the total volume of the solutions being 95 to 100% of the absorptive capacity of the catalyst support, (2) precipitating water-insoluble palladium and gold compounds on the carrier by soaking the impregnated carrier in a solution of an alkali metal silicate, the amount of alkali metal silicate being such that, after the alkali metal silicate has been in contact with the carrier for 12 to 24 hours, the pH of the solution is from 6.5 to 9.5; (3) converting the water-soluble palladium and gold compounds into palladium and gold metal by treatment with a reducing agent; (4) washing with water; (5) contacting the catalyst with alkali metal acetate and (6) drying the catalyst. Using this method, catalysts having a specific activity of at least 83 grams of vinyl acetate per gram of precious metal per hour measured at 150° C. can allegedly be obtained. Shell impregnated catalyst are also disclosed in U.S. Pat. No. 4,087,622. Finally, U.S. Pat. No. 5,185,308 also discloses shell impregnated Pd-Au catalyst and the process of manufacture. Each of the above patents is primarily concerned with the manufacture of fixed bed catalyst useful in the manufacture of vinyl acetate.

It would be economically beneficial if the manufacture of vinyl acetate could be performed in a fluid bed process as well as a fixed bed. However, until the discovery of the process of the present invention the preparation of Pd-Au catalyst in fluid bed form of a Pd-Au catalyst has not led to a catalyst having the necessary properties which can lead to a viable economic fluid bed process for the manufacture of vinyl acetate.

SUMMARY OF THE INVENTION

It is the primary object of the present invention to provide a process for the manufacture of a Pd-Au-alkali metal promoted catalyst useful in the manufacture of vinyl acetate.

It is another object of the present invention to provide a process of manufacturing a fluid bed Pd-Au-alkali metal promoted catalyst useful in the manufacture of vinyl acetate.

It is still another object of the present invention to provide a fluid bed process for the manufacture of vinyl acetate.

Additional objects and advantages of the invention will be set forth in part in the description which follows and in part will be obvious from the description or may be learned by practice of the invention. The objects and advantages of the invention may be realized and attained by means of the instrumentalities and combinations particularly pointed out in the appended claims.

To achieve the foregoing objects of the present invention, the process for manufacture of a Pd-Au-alkali metal (preferably K) catalyst used in the manufacture of vinyl acetate comprises impregnating a preformed support with solution comprising a hydroxy-free metal salt of Pd and Au substantially free of barium and halide, reducing the metal salts to form a deposit of Pd and Au on the surface of the support and impregnating said support with a halide-free metal salt of the alkali metal. In the case of the preparation of the fluid bed form of the catalyst the preformed support is in the form of microspheroidal particles.

In a preferred embodiment of the present invention the metal salt of potassium is added to the solution comprising the salts of Pd and Au.

A still further preferred embodiment of the present invention comprises drying the support impregnated with the metal salt solution of Au and Pd prior to reduction of the metal salts to Au and Pd.

In another preferred embodiment of the present invention the metal salt solution of Au and Pd are prepared to provide a weight ratio of Au to Pd on said resulting catalyst of between 0.10 to 1.00, more preferably 0.2 to 0.8 and especially preferred being 0.25 to 0.75. The specific details of preparation of the salt solutions is conventional and well within the skill of one having ordinary skill in the art. See, for example, U.S. Pat. No. 5,185,308 herein incorporated by reference.

It is another aspect of the present invention to provide a fluid bed process for producing vinyl acetate which comprises contacting in the gaseous state a mixture of $O_2$, $N_2$, ethylene and acetic acid at an elevated temperature and pressure in the presence of a fluid bed catalyst comprising a microspheroidal support having Au, Pd and K impregnated thereon.

In a preferred embodiment of this aspect of the present invention the process for producing vinyl acetate is performed at a temperature between 130° to 170°, preferably 140° to 160° especially preferred being 145° to 155° C.

In another preferred aspect of the present invention the reaction is performed at a pressure of between 100 to 140 psig, preferably 105 to 130 psig, especially preferred being 110 to 125 psig.

DETAILED DESCRIPTION OF THE INVENTION

Reference will now be made in detail to the present preferred embodiments of the invention of which the following examples are set forth for illustrative purposes only.

It has been demonstrated that Pd/Au/K catalyst can be obtained by employing the novel procedure set forth below. The procedure comprises impregnating a support with a solution comprising a hydroxy-free metal salt of Pd and Au substantially free of halide and barium, reducing the metals to deposit Pd and Au on the surface of the support and impregnating the support with a halide-free metal salt of an alkali metal. The metal reduction can be done inside and/or outside the reactor. A variety of reducing agents, such as hydrogen, ethylene, propylene (and any other saturated and unsaturated hydrocarbon), methanol, ethanol etc., can be used. Any non-halide barium-free compound of palladium and gold can be used for the preparation of the Pd/Au/K fluid bed catalysts. Preferably, dimethyl gold acetate, palladium nitrate/palladium acetate and potassium acetate are utilized.

In the practice of the present invention suitable support material include silica, alumina, zirconia or mixtures thereof.

Fluid bed catalysts, prepared by this procedure have been demonstrated as very effective for the production of vinyl acetate by reacting ethylene, oxygen, nitrogen and acetic acid. Typical feed ratios are between 0.05–0.4 $O_2$: 0.2–0.7 $N_2$: 1.0 $C_2H_4$:0.05–0.5 $CH_3COOH$, preferably 0.08 –0.35 $O_2$: 0.25–0.65 $N_2$: 1.0 $C_2H_4$: 0.07–0.35 $CH_3COOH$, especially preferred being 0.1–0.3 $O_2$: 0.3–0.6 $N_2$: 1.0 $C_2H_4$:0.1–0.3 $CH_3COOH$.

EXPERIMENTAL

In the examples which follow the reaction was conducted at the following feed ratio: $0.15O_2/0.54N_2/1.0C_2H_4/0.2CH_3COOH$. The reactor pressure was 115 to 120 psig and the reaction temperature was 150° C.

All catalyst tested were in fluid bed form. A pre-run period of 1 hour preceded sample collection. The beginning of the run was marked by the diversion of product flow from the pre-run vessel to the run vessel. The entire collection system was maintained at reaction pressure and 24° C. The effluent gas was then sampled via gas gun and diverted into a scrubber for the collection of any product which may have escaped uncondensed in the upstream collection vessel. The gas was analyzed on a Carle 400 G.C. The liquid was analyzed on a Hewlett Packard 5710 G.C.

The following examples are illustrative of our invention.

EXAMPLE 1 (comparative)

Weighted 15g of microspheroidal silica (consisted of 70% <88μ on 44μ, 25% <44μ, 5% <105μ on 88μ). Added 10.7 cc of water solution (which contains 0.3 g $Na_2PdCl_4$, and 0.088 g of $HAuCl_4$), and mixed well with glass rod. Permitted to set covered for 30 minutes. Then added 18 ml of water solution of sodium silicate (0.83 g). The obtained mixture was left over night. Then added 1.0 g of hydrazine hydrate and permitted to set for another day. Next morning removed metal from reduced catalyst. Placed separated catalyst in a coarse fritted filter funnel and washed catalyst with 3 liters of $H_2O$. Then the washed catalyst was dried in the oven at 60° C. Metal analysis has given Pd 0.16% (instead of 0.6%), Au 0.072% (instead of 0.25%). Then the catalyst (6.75 g) was impregnated with 6.7 ml of water solution of potassium acetate (0.1 g). Finally, the catalyst was dried in the oven overnight at 60° C.

The fluid bed catalyst was tested for ethylene acetoxylation. The obtained results are given in Table 1.

Example 2

Weighted 0.054 g of dimethyl gold acetate and dissolved it in 1.0 g of $CH_3COOH$. Added 6.0 g of $H_2O$ followed by palladium nitrate (0.39 g). The obtained solution was impregnated to 15 g of microspheroidal silica. The obtained catalyst was dried at 60° C. overnight. Then the catalyst was reduced with 50/50 $H_2/N_2$ mixture (~100 cc/min) at 160° C. overnight. The obtained catalyst (13 g) was then impregnated with 0.7 g of potassium acetate dissolved in 6 ml of $H_2O$, and the catalyst was dried at 60° C. overnight. Metal analysis has given Pd 0.95% (instead of 0.9%) Au 0.25% (instead of 0.25%). The fluid bed catalyst was tested for ethylene acetoxylation. The obtained results are given in Table 1.

Example 3

Palladium acetate (0.302g), dimethyl gold acetate (0.14 g), potassium acetate (0.9g) were dissolved in 9.3 cc of acetic acid by heating at 60° C. The cleared solution was impregnated to 15 g of microspheroidal silica. The obtained catalyst was dried at 60° C. overnight. Then the catalyst was reduced with 50/50 $H_2/N_2$ mixture (~100 cc/min.) at 160° C. overnight.

The fluid bed catalyst was tested for ethylene acetoxylation. The obtained results are given in Table 1.

TABLE 1

| Example Number | Catalyst | Support Used | *STY | Selectivity To VA |
|---|---|---|---|---|
| 1 (comparative) | Pd—Au—K | Microspheroidal Silica | 57 | 92.0 |
| 2 | Pd—Au—K | Microspheroidal Silica | 464 | 93.8 |
| 3 | Pd—Au—K | Microspheroidal Silica | 497 | 93.1 |

*STY = grams of vinyl acetate/per liter of catalyst/per hour.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What we claim as our invention is:

1. A process for the manufacture of a Au/Pd/Alkali metal containing fluid bed catalyst useful in the manufacture of vinyl acetate comprising impregnating a support with a solution comprising an hydroxy-free metal salt of Pd and Au substantially free of barium and halide selected from the group consisting of dimethyl gold acetate, palladium nitrate and palladium acetate and mixtures thereof, reducing the metal salts to form a deposit of Pd and Au on the surface of the support and impregnating the support with a halide-free metal salt of the alkali metal.

2. The process of claim 1, wherein the support impregnated with the metal salts of Pd and Au is dried prior to reduction.

3. The process of claim 1, wherein the support is selected from the group consisting of alumina, silica and zirconia.

4. The process of claim 1, wherein the weight ratio of Au:Pd on said support is between 0.1 to 1.00.

5. The process of claim 1 wherein said alkali metal is potassium.

6. The process of claim 1 wherein said support is in the form of microspheroidal particles.

7. The process of claim 6 wherein said support is selected from the group consisting of alumina, zirconia and silica.

8. A process for the manufacture of a Au/Pd/Alkali metal containing catalyst used in the manufacture of vinyl acetate comprising impregnating a support with a solution comprising an hydroxy-free metal salt of Pd, Au and alkali metal substantially free of barium and halide selected from the group consisting of dimethyl gold acetate, palladium nitrate and palladium acetate and mixtures thereof, drying the impregnated support, and reducing said metal salts to deposit Pd, Au and alkali metal on the surface of said support.

9. The process of claim 8 wherein the support is in the form of microspheroidal particles.

10. The process of claim 9, wherein the microspheroidal support particles are selected from the group consisting of alumina, silica and zirconia.

11. The process of claim 9, wherein the weight ratio of Au:Pd on said support is between 0.1 to 1.00.

12. The process of claim 9 wherein said alkali metal is potassium.

* * * * *